United States Patent
Al-Hajri et al.

(10) Patent No.: US 11,867,027 B2
(45) Date of Patent: Jan. 9, 2024

(54) CALCIUM CARBONATE SCALE PREDICTION AND INHIBITION IN HYDROCARBON WELLS USING MACHINE LEARNING

(71) Applicant: Saudi Arabian Oil Company, Dhahran (SA)

(72) Inventors: Nasser Mubarak Al-Hajri, Abqaiq (SA); Abdullah Abdulaziz AlGhamdi, Abqaiq (SA); Fahad Muhammed Al-Meshal, Khobar (SA)

(73) Assignee: Saudi Arabian Oil Company, Dhahran (SA)

(*) Notice: Subject to any disclaimer, the term of this patent is extended or adjusted under 35 U.S.C. 154(b) by 1033 days.

(21) Appl. No.: 16/410,690

(22) Filed: May 13, 2019

(65) Prior Publication Data
US 2020/0364623 A1 Nov. 19, 2020

(51) Int. Cl.
*G01N 33/24* (2006.01)
*E21B 37/00* (2006.01)
(Continued)

(52) U.S. Cl.
CPC .............. *E21B 37/00* (2013.01); *C01F 11/18* (2013.01); *G01N 33/241* (2013.01);
(Continued)

(58) Field of Classification Search
CPC .. E21B 49/08; E21B 2200/22; C02F 2303/22; G06N 3/045; G06N 3/08;
(Continued)

(56) References Cited

U.S. PATENT DOCUMENTS

| | | | | |
|---|---|---|---|---|
| 3,867,286 A | * | 2/1975 | Quinlan | .............. C02F 1/50 210/764 |
| 6,355,771 B1 | * | 3/2002 | Oda | ..................... C23F 14/02 252/175 |

(Continued)

FOREIGN PATENT DOCUMENTS

CN 102603086 7/2012

OTHER PUBLICATIONS

Zhang et al., Oil Field Mineral Scale Control, Jun. 5, 2015 (online) [retrieved Jun. 15, 2022], Mineral Scales and Deposits, pp. 603-617. Retrieved: https://www.sciencedirect.com/science/article/pii/B9780444632289000243 (Year: 2015).*

(Continued)

*Primary Examiner* — Tom Y Lu
*Assistant Examiner* — Dennis Rosario
(74) *Attorney, Agent, or Firm* — Fish & Richardson P.C.

(57) ABSTRACT

Methods for prediction and inhibition of calcium carbonate scale in hydrocarbon wells using machine learning include extracting training data including parameters from aqueous samples. Each aqueous sample is collected from a respective hydrocarbon well. The training data is classified in accordance with hydrocarbon production conditions of each hydrocarbon well. The classified training data is labeled in accordance with whether calcium carbonate scale has formed in each aqueous sample within a particular time period. A feature vector is determined from the labeled training data based on the parameters extracted from each aqueous sample. The feature vector is indicative of whether the respective hydrocarbon well contains calcium carbonate scale. A trained machine learning model is generated, wherein the machine learning model is trained based on the feature vector, to predict a number of the hydrocarbon wells (Continued)

containing calcium carbonate scale within the particular time period.

20 Claims, 5 Drawing Sheets

(51) Int. Cl.
| | |
|---|---|
| G06N 20/10 | (2019.01) |
| C01F 11/18 | (2006.01) |
| G06F 18/214 | (2023.01) |
| G06F 18/2411 | (2023.01) |
| G06N 7/01 | (2023.01) |

(52) U.S. Cl.
CPC ...... *G06F 18/2155* (2023.01); *G06F 18/2411* (2023.01); *G06N 7/01* (2023.01); *G06N 20/10* (2019.01); *E21B 2200/22* (2020.05)

(58) Field of Classification Search
CPC ........ G06N 20/00; G06N 20/10; G06N 20/20; G06F 18/24; G06F 40/30; G06F 18/241; G06F 16/35; G06F 30/27; G06F 2218/12; G06F 16/285; G06F 18/2155; G06F 16/906; G06F 40/169; G06F 16/55; G06F 18/2411; G06F 16/29; G06V 10/82; G06V 10/764; G06V 20/698; G06V 40/172; G06V 20/00; G06V 20/41; G06V 20/10; G06V 20/05; G06V 20/13; G06V 10/7753; G06V 30/19173; G06V 20/70; G06V 20/60; G06V 10/70; G06V 2201/06; G06V 20/188; G06V 20/35; G06V 10/809; G06V 40/197; G06T 2207/20081; G06T 2207/20084; G06T 7/0004; G06T 2207/30164; G06T 2207/30188; G06T 2207/30181; G06T 2207/10032; G06T 2219/004; G06Q 10/06315; G06Q 10/04; G06Q 10/0635; G06Q 30/02; G06Q 30/06; G06Q 30/0202; G06Q 50/02; G06Q 10/0639; G06Q 10/06313; G06Q 50/06; G01N 33/241

See application file for complete search history.

(56) References Cited

U.S. PATENT DOCUMENTS

| | | | |
|---|---|---|---|
| 7,332,459 | B2 | 2/2008 | Collins et al. |
| 2011/0035154 | A1* | 2/2011 | Kendall .................. C04B 28/10 422/111 |
| 2013/0096899 | A1 | 4/2013 | Usadi |
| 2014/0030306 | A1* | 1/2014 | Polizzotti .................. C02F 1/50 424/420 |
| 2015/0356210 | A1 | 12/2015 | Syed et al. |
| 2020/0355838 | A1 | 11/2020 | Venna et al. |

OTHER PUBLICATIONS

Droguett et al., Variable selection and uncertainty analysis of scale growth rate under pre-salt oil wells conditions using support vector regression, May 14, 2014 [retrieved Jun. 15, 2022], Proceedings of the Institution of Mechanical Engineers, Part O: Journal of Risk and Reliability, (Year: 2014).*
[item V continued] vol. 229, issue: 4, pp. 319-326. Retrieved: https://journals.sagepub.com/doi/full/10.1177/1748006X14533105 (Year: 2014).*
Chapelle et al., Choosing Multiple Parameters for Support Vector Machines, Jan. 2002 [retrieved Jun. 15, 2022], Machine Learning, vol. 46, pp. 131-159. Retrieved: https://link.springer.com/article/10.1023/A:1012450327387 (Year: 2002).*
Wang et al., Support Vector Machine Algorithm for Automatically Identifying Depositional Microfacies Using Well Logs. Mar. 31, 2019 [retrieved Feb. 10, 2023], sustainability, vol. 11, Issue 7,15 pages. Retrieved: https://www.mdpi.com/2071-1050/11/7/1919 (Year: 2019).*
Huang et al., Using Support Vector Regression for Classification, Oct. 2008 [retrieved Mar. 9, 2023], Advance Data Mining and Applications, Lecture Notes in Computer Science vol. 5139, pp. 581-588. Retrieved: https://link.springer.com/chapter/10.1007/978-3-540-88192-6_59 (Year: 2008).*
Ahmadi et al., "A rigorous model to predict the amount of dissolved calcium carbonate concentration throughout oil field brines: side effect of pressure and temperature," Fuel, Jan. 2015, 139:154-159.
Arash et al., "Rigorous modeling for prediction of barium sulfate (barite) deposition in oilfield brines," Fluid Phase Equilibria, Elsevier, Jan. 2014, 366:117-126.
Foroutan et al., "A neural network approach to predict formation damage due to calcium sulphate precipitation," presented at the SPE European Formation Damage Conference and Exhibition, The Netherlands, Jun. 5-7, 2013, 12 pages.
PCT International Search Report and Written Opinion in International Appln. No. PCT/US2020/032627, dated Aug. 7, 2020, 15 pages.
Kamari et al., "Determination of the equilibrated calcium carbonate (calcite) scaling in aqueous phase using a reliable approach," Journal of the Taiwan Institute of Chemical Engineers, 2014, 45:1307-1313, 7 pages.
Paz et al., "Prediction of calcium carbonate scaling in pipes using artificial neural networks," Proceedings of the ASME 2017 36th International Conference on Ocean, Offshore, and Arctic Engineering, Trondheim, Norway, Jun. 2017, 10 pages.
GCC Examination Report issued in Gulf Cooperation Council Appln. No. 2020-39732, dated Jul. 31, 2021, 5 pages.
GCC Examination Report issued in Gulf Cooperation Council Appln. No. 2020-39734, dated Jul. 31, 2021, 3 pages.
GCC Examination Report in Gulf Cooperation Council Appln. No. GC 2020-39732, dated Nov. 30, 2021, 4 pages.
PCT International Search Report and Written Opinion in International Appln. No. PCT/US2020/032626, dated Sep. 8, 2020, 14 pages.
Bahadori, "Estimation of Potential Precipitation From an Equilibrated Calcium Carbonate Aqueous Phase Using Simple Predictive Tool," Society of Petroleum Engineers, SPE 132403-PA, SPE Projects, Facilities and Construction, vol. 6, Issue 4, Dec. 2011, 8 pages.
Hamid et al., "A Practice Method of Prediction Calcium Carbonate Scale Formation in Well Completions," Society of Petroleum Engineers, SPE 168087-PA, SPE Production and Operations, vol. 31, Issue 1, Feb. 2016, 11 pages.
Larson and Buswell, "Calcium Carbonate Saturation Index and Alkalinity Interpretations," State of Illinois, Cicular No. 22, Department of Registration and Education State Water Survey Division, Urbana Illinois, reprinted from the American Water Works Association vol. 34, No. 11, Nov. 1942, 1943, 15 pages.
Stiff et al., "A Method of Predicting the Tendency of Oil Field Waters to Deposit Calcium Carbonate," Society of Petroleum Engineers, Journal of Petroleum Technology, SPE-952213-G, vol. 4, Issue 9, Sep. 1952, 4 pages.
Vetter et al., "Calcium Carbonate Scale in Oilfield Operations," Society of Petroleum Engineers, SPE Annual Technical Conference and Exhibition, Dallas Texas, SOE-16908-MS, Sep. 27-30, 1987, 16 pages.
Yeboah et al., "A New and reliable Model for Predicting Oilfield Scale Formation," Society of Petroleum Engineers, SPE International Symposium on Oilfield Chemistry, New Orleans, Louisiana, SPE 25166-MS, Mar. 2-5, 1993, 10 pages.
GCC Examination Report in Gulf Cooperation Council Appln. No.GC 2020-39734, dated Dec. 31, 2021, 3 pages.

* cited by examiner

300

```
┌─────────────────────────────────────────────────────────────────┐
│ Extract, using a computer system, training data including one   │
│ or more parameters from each aqueous sample of a plurality of   │
│ aqueous samples, wherein the each aqueous sample is collected   │
│ from a respective hydrocarbon well of a plurality of            │
│ hydrocarbon wells                                               │
│ 304                                                             │
└─────────────────────────────────────────────────────────────────┘
                              ↓
┌─────────────────────────────────────────────────────────────────┐
│ Classify, using the computer system, the training data in       │
│ accordance with hydrocarbon production conditions of each       │
│ hydrocarbon well                                                │
│ 308                                                             │
└─────────────────────────────────────────────────────────────────┘
                              ↓
┌─────────────────────────────────────────────────────────────────┐
│ Label, using the computer system, the classified training data  │
│ in accordance with whether calcium carbonate scale has formed   │
│ in each aqueous sample of the plurality of aqueous samples      │
│ within a particular time period                                 │
│ 312                                                             │
└─────────────────────────────────────────────────────────────────┘
                              ↓
┌─────────────────────────────────────────────────────────────────┐
│ Determine, using the computer system, a feature vector from     │
│ the labeled training data based on the one or more parameters   │
│ extracted from the each aqueous sample of the plurality of      │
│ aqueous samples, wherein the feature vector is indicative of    │
│ whether the respective hydrocarbon well contains calcium        │
│ carbonate scale                                                 │
│ 316                                                             │
└─────────────────────────────────────────────────────────────────┘
                              ↓
┌─────────────────────────────────────────────────────────────────┐
│ Generate, using the computer system, a trained machine learning │
│ model, wherein the machine learning model is trained based on   │
│ the feature vector, to predict a number of hydrocarbon wells of │
│ the plurality of hydrocarbon wells containing calcium carbonate │
│ scale within the particular time period                         │
│ 320                                                             │
└─────────────────────────────────────────────────────────────────┘
```

For each machine learning method of a plurality of machine learning methods: generate, using a computer system, a confusion matrix by executing a machine learning model trained, using the machine learning method, to predict a number of hydrocarbon wells containing calcium carbonate scale, wherein the machine learning model is trained based on parameters extracted from a plurality of aqueous samples collected from a total number of hydrocarbon wells
404

Generate, using the computer system, a probabilistic model indicating an uncertainty associated with using the machine learning method to predict the number of hydrocarbon wells containing calcium carbonate scale based on the confusion matrix
408

Generate, using the computer system, a cost metric indicating a cost of implementing a calcium carbonate scale inhibition program using the machine learning method based on the probabilistic model
412

Select a machine learning method of the plurality of machine learning methods having a lowest cost metric
416

Determine, using the computer system, whether the lowest cost metric is less than a base cost of implementing the calcium carbonate scale inhibition program for the total number of hydrocarbon wells using a calcium carbonate scale inhibition chemical
420

Responsive to the lowest cost metric being less than the base cost, presenting, using a display device of the computer system, the machine learning method having the lowest cost metric
424

FIG. 4

CALCIUM CARBONATE SCALE PREDICTION AND INHIBITION IN HYDROCARBON WELLS USING MACHINE LEARNING

TECHNICAL FIELD

This description relates generally to prediction and inhibition of calcium carbonate scale, for example, to prediction and inhibition of calcium carbonate scale in hydrocarbon wells using machine learning.

BACKGROUND

Calcium carbonate scale can form in hydrocarbon wells when brine and oil mix in a reservoir or wellbore. When calcium carbonate scale forms in a hydrocarbon well, the scale can coat perforations, casings, or other equipment, such as safety equipment or gas lift mandrels. The scale formation can impact production and require clean out or descaling of the hydrocarbon well.

SUMMARY

Methods for prediction and inhibition of calcium carbonate scale in hydrocarbon wells using machine learning are disclosed. In some embodiments, the methods include using a computer system to extract training data including one or more parameters from each aqueous sample of a plurality of aqueous samples. Each aqueous sample is collected from a respective hydrocarbon well of a plurality of hydrocarbon wells. The computer system classifies the training data in accordance with hydrocarbon production conditions of each hydrocarbon well. The computer system labels the classified training data in accordance with whether calcium carbonate scale has formed in each aqueous sample of the plurality of aqueous samples within a particular time period. The computer system determines a feature vector from the labeled training data based on the one or more parameters extracted from each aqueous sample of the plurality of aqueous samples. The feature vector is indicative of whether the respective hydrocarbon well contains calcium carbonate scale. The computer system generates a trained machine learning model, wherein the machine learning model is trained based on the feature vector, to predict a number of hydrocarbon wells of the plurality of hydrocarbon wells containing calcium carbonate scale within the particular time period.

These and other aspects, features, and implementations can be expressed as methods, apparatus, systems, components, means, or steps for performing a function, and in other ways.

These and other aspects, features, and implementations will become apparent from the following descriptions, including the claims.

BRIEF DESCRIPTION OF THE DRAWINGS

FIG. 3 shows a process for prediction of calcium carbonate scale in hydrocarbon wells using machine learning, in accordance with one or more embodiments.

FIG. 4 shows a process for inhibition of calcium carbonate scale in hydrocarbon wells using machine learning, in accordance with one or more embodiments.

DETAILED DESCRIPTION

Figure 1:
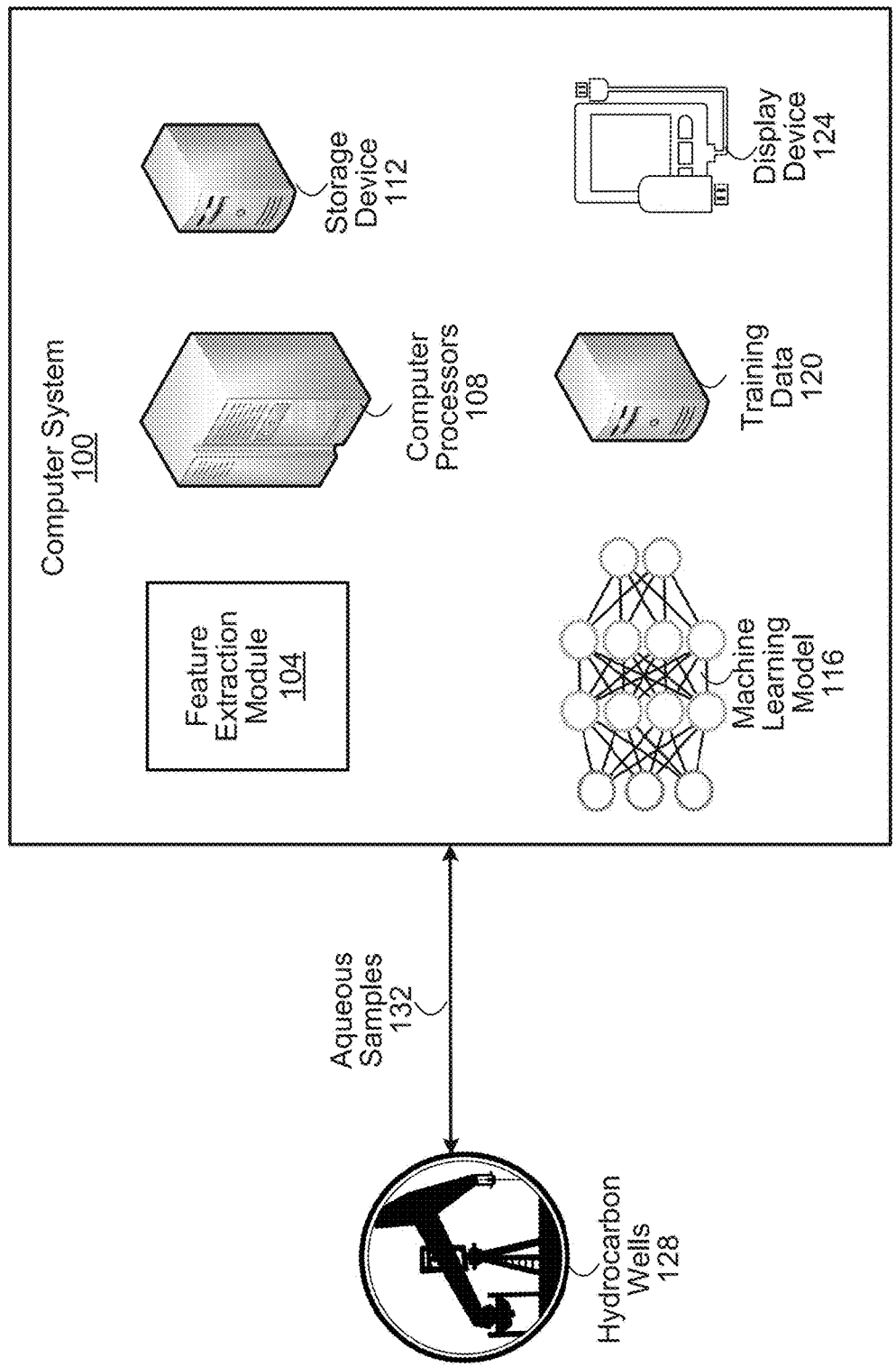
FIG. 1 illustrates a computer system for prediction and inhibition of calcium carbonate scale in hydrocarbon wells using machine learning, in accordance with one or more embodiments.

Methods of predicting and inhibiting calcium carbonate ($CaCO_3$) scale in hydrocarbon wells using machine learning are disclosed. Calcium carbonate scale formation can occur in oilfield operations as a result of the hydrocarbon production conditions and a shift in the chemical equilibrium of the contents of the hydrocarbon wells. When fluids such as brine, oil, and gas mix in a hydrocarbon reservoir or wellbore under different thermodynamic, kinetic, or hydrodynamic conditions, different amounts of calcium carbonate scale can be formed at different points in time. To predict the formation of calcium carbonate scale in hydrocarbon wells, aqueous samples including a mixture of oil and brine are collected. A computer system is used to extract one or more parameters indicating a level of chemical equilibrium from the aqueous samples. The extracted parameters are used to create training data to train a machine learning model to predict calcium carbonate scale. The training data is classified in accordance with hydrocarbon production conditions of each hydrocarbon well such as a hydrocarbon flow rate, a hydrocarbon pressure, a temperature of the hydrocarbon well, or a composition of brine, oil, and gas of the hydrocarbon well. The classified training data is labeled using the computer system in accordance with whether calcium carbonate scale has formed in the aqueous samples within a particular time period. The labeled training data is used to determine a feature vector based on the parameters extracted from the aqueous samples. The feature vector indicates to the machine learning model whether a hydrocarbon well contains calcium carbonate scale. The machine learning model is thus trained based on the feature vector to predict a number of hydrocarbon wells that contain calcium carbonate scale.

The trained machine learning model can be used to determine which of several machine learning methods provides the lowest cost for implementing a calcium carbonate scale inhibition program for hydrocarbon wells. For example, a k-nearest neighbors method, a support vector machine method, a gradient boosting method, a gradient boosting classifer method, or a decision tree classifier method can be used. The trained machine learning model is executed using several machine learning methods to generate a confusion matrix. The confusion matrix indicates the number of hydrocarbon wells for which the machine learning correctly predicted the presence or absence of calcium carbon scale formation. A probabilistic model is generated based on the confusion matrix to indicate an uncertainty associated with using each machine learning method to predict the number of hydrocarbon wells containing calcium carbonate scale. A cost metric that indicates a cost of implementing a calcium carbonate scale inhibition program using each machine learning method is generated based on the probabilistic model. The machine learning method that provides the lowest cost metric is selected. It is determined whether the lowest cost metric is less than a base cost of implementing the calcium carbonate scale inhibition program. The base cost refers to the cost for treating all the hydrocarbon wells using a calcium carbonate scale inhibition chemical. If the lowest cost metric is less than the base cost, the machine learning method having the lowest cost metric is presented on a display device.

Among other benefits and advantages of the embodiments disclosed, the methods provide an integrated and flexible calcium carbonate scale prediction architecture from hydrocarbon data collection to training and execution of a machine learning model. Furthermore, the methods include a probabilistic framework to design an efficient and effective oilfield-wide calcium scale inhibition program. Prediction of the calcium carbonate scale formation using an accurate machine learning model reduces computational power. The cost of designing a calcium carbonate scale inhibition program is thus reduced using the procedural workflow that alternates different machine learning classification and probability models to achieve a global cost minima.

Computer System for Prediction of Calcium Carbonate Scale in Hydrocarbon Wells

FIG. 1 illustrates a computer system 100 for prediction and inhibition of calcium carbonate scale in hydrocarbon wells 128 using machine learning, in accordance with one or more embodiments. Among other components and parts, FIG. 1 illustrates the hydrocarbon wells 128, aqueous samples 132, and the computer system 100. The hydrocarbon wells 128 are communicably coupled to the computer system 100 over a network (e.g., the Internet 528 or the local network 522 illustrated and described below with reference to FIG. 5).

The hydrocarbon wells 128 are borings in the earth that are constructed to bring petroleum oil hydrocarbons and natural gas to the surface. The hydrocarbon wells 128 are enabled to produce oil or gas by implementing perforations (or other means such as open hole completions) to provide a path for the oil to flow from the surrounding rock into the production tubing. Acids and fracturing fluids may be pumped into a hydrocarbon well 128 to stimulate the reservoir rock to optimally produce hydrocarbons. The hydrocarbon production conditions of the hydrocarbon wells 128 can affect the location, amount, and time period of calcium carbonate (CaCO3) scale formation. For example, the hydrocarbon flow rate, hydrocarbon pressure, and composition of the brine, oil, and gas in a hydrocarbon well affects the chemical equilibrium of the contents of the well and therefore affects the calcium carbonate scale formation. The hydrocarbon production conditions at different locations in the production system can also change as a function of location and time during the production operation within an oilfield.

The hydrocarbon wells 128 can have aqueous zones lying under the hydrocarbons or sometimes in the same zone as the oil and gas. The hydrocarbon well 128 can thus produce water or brine as a byproduct along with the oil and gas. To predict the formation of calcium carbonate scale in the hydrocarbon wells 128, the aqueous samples 132 are collected from the hydrocarbon wells 128. The aqueous samples 132 can include water, brine, and minerals. In some embodiments, the computer system 100 is communicably coupled to the hydrocarbon wells 128 to receive the aqueous samples 132 from the hydrocarbon wells 128 for extracting parameters from the aqueous samples 132. In other embodiments, the extraction of the parameters from the aqueous samples 132 can be performed locally at the hydrocarbon wells, and the parameters can be communicated to the computer system 100 for scale prediction.

The computer system 100 is used to train a machine learning model to predict a number of the hydrocarbon wells 128 containing calcium carbonate scale. An implementation of the computer system 100 is illustrated and described below with reference to FIG. 5. The computer system includes feature extraction module 104, one or more computer processors 108, a storage device 112, a machine learning model 116, training data 120, and a display device 124. The computer processors 108 are computer hardware used to perform the methods disclosed herein. The computer processors 108 are illustrated and described below with reference to FIG. 5. The storage device 112 is used to store data (e.g., the parameters extracted from the aqueous samples 132) and instructions to perform the methods disclosed herein. The storage device 112 is illustrated and described below with reference to FIG. 5.

The aqueous samples 132 are used to extract the training data 120 for the machine learning model 116. In some embodiments, the training data 120 is stored on the storage device 112. The training data 120 extracted from the aqueous samples 132 includes one or more parameters. The parameters extracted from the aqueous samples 132 can include the ionic composition of the aqueous samples. For example, the ionic composition can include the molar concentration of the calcium cation $Ca^{2+}$ (expressed in mole/L), the molar concentration of the Sodium ion $Na^+$, or the molar concentration of the bicarbonate ion $HCO3^-$. The parameters extracted from an aqueous sample 132 can include the negative of the base 10 logarithm of the molar concentration of hydrogen ions $H^+$ in the aqueous sample 132 (denoted as PH). In some embodiments, a collection date of the aqueous sample and a calcium carbonate scale inspection date is added to the training data 120 to verify the calcium carbonate scale tendency prediction results. In some embodiments, a calcium carbonate scale formation event is recorded within the training data 120 to denote whether calcium carbonate scale has precipitated in each aqueous sample or not based on the inspection results.

The computer system 100 classifies the training data 120 in accordance with hydrocarbon production conditions of each hydrocarbon well 128. The classification of the training data 120 is performed to achieve similarity in the hydrocarbon production conditions such as a flow rate or a pressure drop across the hydrocarbon wells 128 to improve the usefulness of the training data 120. In some embodiments, the training data 120 is grouped by hydrocarbon well based on the production performance and water cut (ratio of water compared to the volume of total liquids produced) of the hydrocarbon well. In some embodiments, the training data 120 is classified in accordance with the hydrocarbon flow rate, the hydrocarbon pressure, or the temperature of each hydrocarbon well. The flow rate, pressure, and temperature affect the equilibrium level and thus calcium carbonate scale formation. In some embodiments, the training data 120 is classified in accordance with the composition of brine, oil, and gas of the hydrocarbon wells 128. For example, the brine and oil compositions can be used for classification prior to, during, and after the reservoir fluids have been exposed to temperature or pressure changes. In some embodiments, the training data 120 is classified in accordance with the bubble point and flash behavior of the three-phase oil/brine/gas system as a function of pressure and temperature. In some embodiments, the training data 120 is classified in accordance with a distribution of $CO_2$ between the oil and brine phases, and the variations of the $CO_2$ partitioning prior to and during production operation. In some embodiments, the training data 120 is classified in accordance with a variation in the water to oil ratio (WOR), the gas to oil ratio (GOR), and the gas to water ratio (GWR) during production operation.

The computer system 100 is used to select and adjust a particular time period that is used for training the machine learning model 116 with the training data 120 for predicting the number of hydrocarbon wells 128 that will develop calcium carbonate scale in the particular time period. The computer system 100 selects the particular time period based on the type of the calcium carbonate scale inhibition chemical used in the calcium carbonate scale inhibition program. The calcium carbonate scale inhibition chemical is used to prevent the formation of the calcium carbonate scale from blocking or hindering fluid flow through the pipelines, valves, or the pumps used in oil production and processing. For example, acrylic acid polymers, maleic acid polymers, or phosphonates can be added to the oil production system to delay, reduce, or prevent scale deposition. In some embodiments, the computer system 100 selects the particular time period based on the chemical residue life of the calcium carbonate scale inhibition chemical. In other embodiments, the computer system 100 selects the particular time period based on the calcium carbonate scale inhibition program design criteria, scale inhibition economics, or the size of the oilfield. In some embodiments, a time period of 10 years can be selected.

The computer system 100 labels the classified training data 120 in accordance with whether calcium carbonate scale has formed in the aqueous samples 132 within the particular time period. For example, a scaling event in the training data 120 can be denoted by "1" if calcium carbonate scale has occurred in a hydrocarbon well 120 within a particular number of years. The scaling event can be denoted by "0" if calcium carbonate scale has not occurred within the particular number of years.

The feature extraction module 104 extracts or determines one or more feature vectors from the training data 120. The feature vectors can be stored in the storage device 112. The feature extraction may be implemented in software using the computer processors 108 or in special-purpose hardware as described below with reference to FIG. 5. The feature extraction module 104 determines the feature vectors from the labeled training data 120 based on the one or more parameters extracted from the aqueous samples 132. Each feature vector can correspond to a respective hydrocarbon well 128 and each feature vector is indicative of whether the respective hydrocarbon well 128 contains calcium carbonate scale.

In some embodiments, a feature vector indicates a level of carbonate equilibrium of an aqueous sample 132 based on the one or more parameters extracted from the aqueous sample 132. The calcium carbonate scale deposit is caused by a shift toward carbonate in the carbonate-bicarbonate-$CO_2$ equilibrium. When the equilibrium shifts away from carbonate, the precipitation goes back into solution. The chemical equilibrium is the state in which both the reactants and products are present in concentrations which have no further tendency to change with time. The chemical equilibrium is thus achieved when the rate of forward reaction is same as the reverse reaction. The precipitated calcium carbonate combines with iron in the water to form a crust that inhibits corrosion. If the water tends to dissolve carbonate, the scale becomes porous, and electrolytic corrosion takes place. The level of carbonate equilibrium of an aqueous sample 132 is thus indicative of the tendency of calcium carbonate scale formation and the corrosive properties of the calcium carbonate scale.

The feature extraction module 104 reduces redundancy in the training data 120 by transforming the training data 120 into a reduced set of features (the feature vector). The feature vector contains the relevant information from the training data 120, such that features of interest are identified by the machine learning model 116 using the reduced representation instead of the complete training data. For example, the feature extraction module 104 uses the training data 120 to estimate a water saturation level SL of one or more aqueous samples 132. In some embodiments, the water saturation level SL is determined by $$SL = \frac{[Ca^{2+}][CO_3^{2-}]}{K_{sp}}, \text{ where } [Ca^{2+}]$$

denotes the molar concentration of the calcium cation, $[CO_3^{2-}]$ denotes the molar concentration of the carbonate anion, and $K_{sp}$ is the equilibrium constant.

In some embodiments, the feature extraction module 104 uses the training data 120 to estimate a Langelier Saturation Index of one or more aqueous samples 132. The Langelier Saturation Index is related to the conditions of carbonate equilibrium, and can be used to estimate the pH of the aqueous sample 132 at equilibrium. If the actual pH is higher than the estimated pH, the aqueous sample 132 has a tendency to form scale. If the actual pH is lower than the estimated pH, the aqueous sample has a tendency to be corrosive. In some embodiments, the Langelier Saturation Index is related to the pH, calcium concentration, and total alkalinity of the aqueous sample 132. The alkalinity of the aqueous sample 132 refers to the ability of the aqueous sample 132 to neutralize an acid to the equivalence point of calcium carbonate. The alkalinity can be determined by a sum of the ion concentrations $[HCO3^-]+2\times[CO3(-2)]+[OH^-]-[H^+]$. When the Langelier Saturation Index is positive, this is indicative of calcium carbonate scale formation in the aqueous sample 132. When the Langelier Saturation Index is positive, this is indicative of corrosion. In some embodiments, the Langelier Saturation Index is used for aqueous samples 132 having a total solid concentration as high as 4000 ppm.

In some embodiments, the Langelier Saturation Index can be determined by $LSI=PH-PH_S$, where LSI denotes the Langelier Saturation Index, PH denotes the molar concentration of hydrogen ions H+ in the aqueous sample, and PHs denotes the pH value when CaCO3 achieves saturation in the system. The value of PHs can be determined by $PH_S=(9.3+A+B)-(C+D)$. The value of A can be determined by $$A = \frac{(\text{Log}_{10}(TDS) - 1)}{10},$$

where TDS denotes the amount of total dissolved solids. The value of B can be determined by $=-13.12\times\text{Log}_{10}(T(C)+273)+34.55$, where T(C) refers to the temperature in degrees Celsius. The value of C can be determined by $C=\text{Log}_{10}([Ca^{2+}] \text{ as } CaCO_3)-0.4$, and the value of D can be determined by $D=\text{Log}_{10}(\text{alkalinity as } CaCO_3)$. In some embodiments, the reliability of the Langelier Saturation Index is improved by adjusting for temperature and salinity effects during the CaCO3 precipitation at atmospheric pressure.

In some embodiments, an empirical method is used to extend the application of the Langelier Saturation Index to aqueous samples 132 having a high salt concentration. For example, the formulation (SI=pH−K−pCa−pAlk) can be used, based on the tendency of the oilfield waters, to predict calcium carbonate scale. In this formulation, pCa denotes the negative logarithm of the calcium concentration and pAlk denotes the negative logarithm of the total alkalinity. The value of K can be determined as a function of the ionic strength of the aqueous sample 132 as follows: $\mu=0.5\times(C_1V_1^2+C_2V_2^2+ \ldots +C_nV_n^2)$, where $\mu$ denotes the ionic strength, C denotes the concentration of each ion expressed as gram ions per 1000 gm of solvent, and V denotes a valence of the ion.

In some embodiments, features based on an Oilfield Scale Prediction Model can be used to predict a potential and deposition profile of the calcium carbonate scale based on thermodynamic data and kinetic data. The Oilfield Scale Prediction Model uses experimental solubility data to determine the saturation index. Critical saturation indices beyond which scaling occurs can be used. The Oilfield Scale Prediction Model uses the flow characteristics and experimental kinetic data to predict the calcium carbonate scale deposition profile from the bottomhole to the surface once the critical saturation index is exceeded as follows:

$$SI = \log\frac{[Ca++][HCO3-]^2}{Ksp\,Pco2},$$

where SI denotes the calcium carbonate saturation index, $K_{sp}$ denotes the equilibrium constant, and $P_{CO2}$ denotes the partial pressure of $CO_2$.

In some embodiments, the amounts of flashed gases from the oil and the brine phases, and the effects of the gas distribution (especially $CO_2$) between the oil and brine phases under the reservoir and the production conditions on the $CaCO_3$ scale formation can be used to construct features for the predictive model. In other embodiments, features to predict $CaCO_3$ scale formation under field conditions include the water composition, pressure, temperature, the WOR, the GOR, and the total $CO_2$ and its partitioning between the different liquid phases. In some embodiments, the features used include weight-gain data from coupon tests and a tube-plugging test. Such features can predict the calcium carbonate scale-growth rate at a given point on a solid surface using the pressure, pressure gradient, temperature, fluid velocity, and brine concentration as independent variables.

In some embodiments, the features include a scale-growth field $\dot{y}$ at a given time that can be obtained by integrating a scaling-rate function $\dot{y}=F1F2+F3F4$, where $\dot{y}$ denotes the rate of scale growth at a point on a solid surface. The value of F1 depends on an empirical model F0 derived using an artificial neural network from the scale deposition as a function of five variables (pressure, temperature, brine concentration, velocity, and time). F2 denotes the locations at which calcium carbonate scale is deposited in accordance with the surface position with respect to gravity and whether the surface is concave or convex. The values of F3 and F4 account for boned scaling, which is independent of gravity and a function of the pressure gradient. The model described above can be used to predict calcium carbonate scale formation at inflow control valves (ICVs), allowing for the design of improved completion and fluid-handling systems for pre-salt wells.

In some embodiments, the features used can include the pH, temperature, the ionic strength of an aqueous sample, the calcium cation concentration, the bicarbonate anion concentration, and the $CO_2$ mole fraction when the water mixture is saturated with gas containing $CO_2$ to evaluate the effect of solution conditions on the tendency and extent of precipitation. In some embodiments, concentrations of calcium carbonate from 10 to 10000 mg/L, with temperature ranging from 5 to 90° C., a total ionic strength ranging between 0.1 and 3.6, and pH values ranging from 5.5 and 8 can be used. For example, the natural logarithm of K can be determined by $\ln(K)=a+bI+cI^2+dI^3$, where a, b, c and d are constants, K denotes the correction factor for the total ionic strength and temperature, and I denotes the total ionic strength. Values of pCa=8.922 $(CCa2+)^{-0.2708}$, pAlk=8.1997 $(CHCO3+CO3)^{-0.23638}$, and pHs=pCa-pAlk-K can be used. The natural logarithm of $S_f$ can be determined by $\ln(S_f)=a+bT+cT^2+dT^3$, where $S_f$ denotes the solubility factor and T denotes the temperature. The value of R' can be determined by $(C_{HCO3}\times 0.82)/(X_{CO2}\times S_f)$, where $X_{CO2}$ denotes the CO2 mole fraction in water mixture saturated with a gas containing CO2. The value of pH can be determined by $0.4341\times\ln(R')+6.2964$, where pH denotes the actual pH value in the system. The value of SI can be determined by pH-pH$_S$, where pH$_s$ denotes the pH value when $CaCO_3$ achieves saturation in the system.

In some embodiments, the feature extraction module 104 uses the training data 120 to estimate a Ryznar Saturation Index of the aqueous samples 132 from the labeled training data 120. The Ryznar Saturation Index can be determined by RSI=2PH$_s$−PH. In some embodiments, the feature extraction module 104 uses the training data 120 to estimate a Puckorius Scaling Index of one or more aqueous samples 132 from the labeled training data 120. The Puckorius Scaling Index can be determined by PSI=2PH$_s$−PH$_{eq}$, where PHeq is a variable defined by the Puckorius Scaling Index as $1.465\times\log_{10}$ (Alkalinity)+4.54.

In some embodiments, the following dimensionality reduction techniques can be used by the feature extraction module 104 to reduce a dimensionality of the feature vector: independent component analysis, Isomap, Kernel PCA, latent semantic analysis, partial least squares, principal component analysis, multifactor dimensionality reduction, nonlinear dimensionality reduction, Multilinear Principal Component Analysis, multilinear subspace learning, semidefinite embedding, Autoencoder, and deep feature synthesis.

The machine learning model 116 is a mathematical and connectivity model that is trained using the feature vector to make predictions or decisions without being explicitly programmed. The computer system 100 can use one or more machine learning methods to train the machine learning model 116 using the feature vector. In one embodiments, a k-nearest neighbors method is used. The k-nearest neighbors method can be used for classification and regression. For both classification and regression, the data set consists of the k closest training examples in the feature vector space. In some embodiments, a support vector machine method is used. Support vector machines use supervised learning to train the machine learning model 116 with associated learning algorithms that analyze the feature vector that is used for classification and regression analysis. The machine learning model 116 is presented with a set of training examples, each marked as belonging to one or the other of two categories. The support vector machine method trains the machine learning model 116 to assigns new examples to one category or the other, making it a non-probabilistic binary linear classifier.

In some embodiments, the computer system 100 uses a gradient boosting method to train the machine learning model 116. Gradient boosting is a machine learning method for regression and classification. Gradient boosting generates a trained model in the form of an ensemble of weak prediction models, which are typically decision trees. Gradient boosting trains the machine learning model 116 in a stage-wise fashion similar to other boosting methods. The machine learning model 116 is generalized by optimization of an arbitrary function. In some embodiments, a gradient boosting classifier method is used. A gradient boosting classifier method is a type of boosting algorithm that optimize a cost function over a function space by iteratively selecting a weak hypothesis that points in the negative gradient direction. In some embodiments, a decision tree classifier method is used. Decision tree learning uses a decision tree (as a predictive model) to derive conclusions about an item's target value (represented by the leaves of the tree) based on observations about the item (represented by the branches of the tree). In other embodiments, different machine learning techniques such as linear support vector machine (linear SVM), boosting for other algorithms (e.g., AdaBoost), logistic regression, naïve Bayes, memory-based learning, random forests, bagged trees, boosted trees, boosted stumps, neural networks, or a convolutional neural network (CNN) can be used.

The computer system 100 trains the machine learning model 116, based on the feature vector, to predict a number of the hydrocarbon wells 128 containing calcium carbonate scale within the particular time period. The computer system 100 thus generates the trained machine learning model 116 based on the feature vector. For example, the machine learning model 116 can be thereby configured to determine a score for each hydrocarbon well 128. The score is indicative of a likelihood that the hydrocarbon well 128 has formed calcium carbonate scale by associating the determined features with formation of calcium carbonate scale. In some embodiments, the computer system 100 applies one or more of the machine learning methods described above to train the machine learning model 116 that when applied to new features, outputs indications of whether the features have an associated property or properties, e.g., that when applied to new features, outputs estimates of whether the features have a particular Boolean property or an estimated value of a scalar property.

In some embodiments, the computer system 100 can perform deep learning (also known as deep structured learning or hierarchical learning) to learn data representations, as opposed to using task-specific algorithms. In deep learning, no explicit feature extraction is performed; the features may be implicitly extracted by the computer system 100. For example, the computer system 100 and machine learning model 116 can use a cascade of multiple layers of nonlinear processing units for implicit feature extraction and transformation. Each successive layer uses the output from the previous layer as input. The machine learning model 116 can thus learn in supervised (e.g., classification) and/or unsupervised (e.g., pattern analysis) modes. The machine learning model 116 can learn multiple levels of representations that correspond to different levels of abstraction, wherein the different levels form a hierarchy of concepts.

The computer system 100 executes the trained machine learning model 116 to generate a confusion matrix for each machine learning method. As described above, the machine learning model 116 is trained, using the machine learning method, to predict a number of the hydrocarbon wells 128 containing calcium carbonate scale. The confusion matrix includes a first number X1 of the hydrocarbon wells 128 predicted by the machine learning model 116 to contain calcium carbonate scale, where the first number X1 of the hydrocarbon wells 128 actually contain calcium carbonate scale. The confusion matrix includes a second number X2 of hydrocarbon wells 128 predicted by the machine learning model 116 to contain no calcium carbonate scale, where the second number X2 of the hydrocarbon wells 128 contain calcium carbonate scale.

The confusion matrix includes a third number X3 of hydrocarbon wells 128 predicted by the machine learning model 116 to contain calcium carbonate scale, where the third number X3 of hydrocarbon wells 128 contain no calcium carbonate scale. The confusion matrix includes a fourth number X4 of hydrocarbon wells 128 predicted by the machine learning model 116 to contain no calcium carbonate scale, where the fourth number X4 of hydrocarbon wells 128 contain no calcium carbonate scale. For example, the confusion matrix can be represented as:

|  | Predicted Event: Scale | Predicted Event: No Scale |
|---|---|---|
| Actual Event: Scale | X1 | X2 |
| Actual Event: No Scale | X3 | X4 |

The computer system 100 generates a probabilistic model indicating an uncertainty associated with using each machine learning method to predict the number of hydrocarbon wells 128 containing calcium carbonate scale based on the confusion matrix. The probabilistic model can be used to quantify the uncertainty associated with each machine learning method, if implemented, to select calcium carbonate scale inhibition candidate well. For example, the total number $X_T$ of hydrocarbon wells 128 in the oilfield can be determined by $X_T = X_1 + X_2 + X_3 + X_4$. The probability $P_S$ of scale formation can be determined by $$P_S = \frac{X_1 + X_2}{X_T}.$$

The probability $P_{NS}$ of no scale formation can be determined by $$P_{NS} = \frac{X_3 + X_4}{X_T} = 1 - P_S.$$

The probabilistic model includes a first ratio $P_{CSP}$ of the first number X1 of hydrocarbon wells 128 predicted by the machine learning model 116 to contain calcium carbonate scale to the total number $X_T$ of hydrocarbon wells 128. $P_{CSP}$ denotes the probability of correct scale formation prediction and can be determined by $$P_{CSP} = \frac{X_1}{X_T}.$$

In this case, calcium carbonate scale has actually formed, and the machine learning model 116 correctly predicted the event.

The probabilistic model includes a second ratio $P_{ISP}$ of the second number X2 of hydrocarbon wells 128 predicted by the machine learning model 116 to contain no calcium carbonate scale to the total number $X_T$ of hydrocarbon wells 116. $P_{ISP}$ denotes the probability of incorrect scale formation prediction and can be determined by $$P_{ISP} = \frac{X_2}{X_T}.$$

In this case, scale did form, but the machine learning model 116 did not correctly predict the event. The probabilistic model includes a third ratio $P_{INSP}$ of the third number X3 of hydrocarbon wells 128 predicted by the machine learning model 116 to contain no calcium carbonate scale to the total number $X_T$ of hydrocarbon wells 128. $P_{INSP}$ denotes the probability of incorrect no scale formation prediction and can be determined by $$P_{INSP} = \frac{X_3}{X_T}.$$

In this case, scale has not actually formed, and the machine learning model 116 did not correctly predict the event. The probabilistic model includes a fourth ratio $P_{CNSP}$ of the fourth number X4 of hydrocarbon wells 128 predicted by the machine learning model 116 to contain calcium carbonate scale to the total number $X_T$ of hydrocarbon wells 128. $P_{CNSP}$ denotes the probability of correct no scale formation prediction and can be determined by $$P_{CNSP} = \frac{X_4}{X_T}.$$

In this case, calcium carbonate scale has not actually formed, and the machine learning model 116 correctly predicted the event.

The computer system 100 generates a cost metric $C_P$ indicating a cost of implementing a calcium carbonate scale inhibition program using each machine learning method based on the probabilistic model. The cost model is used to quantify the expected financial impact associated with each machine learning method, if implemented, to select hydrocarbon wells as scale inhibition candidates. A positive sign indicates incurred cost and a negative sign indicates saved or avoided cost.

The metric $C_S$ is used to indicate a cost of removing calcium carbonate scale from a hydrocarbon well after the scale has already formed. The metric $C_T$ is used to indicate a cost of using a scale inhibition chemical to treat a hydrocarbon well before scale has formed. In some embodiments, the cost metric $C_P$ is generated from the cost $C_T$ of implementing the calcium carbonate scale inhibition program for a single hydrocarbon well based on the first ratio $P_{CSP}$ and the fourth ratio $P_{CNSP}$. The expected net saving $C_{CSP}$ obtained by correctly predicting scale formation per well can be determined by $C_{CSP}=P_{CSP}\times(C_T-C_S)$. Thus, correct prediction of a scale formation event (when the machine learning model 116 predicts that scale will form and scale actually forms) avoids the cost of a scale removal operation but incurs the cost of the scale inhibition treatment. The expected savings $C_{CNSP}$ of correctly predicting no scale formation cases per well can be determined by $C_{CNSP}=-P_{CNSP}\times C_T$. The correct predication of no scale formation events within the particular time period (the machine learning model 116 predicted no scale will form and scale has not formed) thus leads to saving the cost of the scale inhibition treatment operation.

In some embodiments, the cost metric $C_P$ is generated from the cost $C_S$ of removing calcium carbonate scale from a single hydrocarbon well 128 based on the second ratio $P_{ISP}$ and the third ratio $P_{INSP}$. The cost $C_{ISP}$ of incorrectly predicted scale formation cases per well can be determined by $C_{ISP}=P_{ISP}\times C_S$. The incorrect predication of a scale formation event (the machine learning model 116 predicted no scale while scale actually formed) thus leads to incurring the cost of the scale removal operation. The cost $C_{INSP}$ of incorrectly predicted no scale formation events per well can be determined by $C_{INSP}=P_{INSP}\times C_T$. The incorrect predication of no scale formation events (the machine learning model 116 predicted scale will form while scale did not form) thus leads to incurring the cost of the scale inhibition treatment. The overall expected net cost metric $C_P$ of the scale inhibition program can thus be determined by $C_P=X_T\times(C_{CSP}+C_{ISP}+C_{CNSP}+C_{INSP})$.

The computer system 100 executes the trained machine learning model 116 using each different machine learning method and uses the probabilistic model to select a machine learning method of the several machine learning methods that has the lowest cost metric $C_P$.

The computer system 100 determines a base cost $C_{BC}$ of implementing the calcium carbonate scale inhibition program for the total number $X_T$ of hydrocarbon wells 128 using the calcium carbonate scale inhibition chemical. In some embodiments, the computer system 100 determines the base cost $C_{BC}$ from the cost $C_T$ of implementing the calcium carbonate scale inhibition program for a single hydrocarbon well, the cost $C_S$ of removing calcium carbonate scale from a single hydrocarbon well 128, and a sum of the first number X1 of hydrocarbon wells 128 predicted by the machine learning model 116 to contain calcium carbonate scale and the second number X2 of hydrocarbon wells 128 predicted by the machine learning model 116 to contain no calcium carbonate scale. For example, the base cost $C_{BC}$ can be determined by $C_{BC}=X_T\times(C_T-P_S\times C_S)$.

The computer system 100 determines whether the lowest cost metric of the machine learning methods is less than the base cost $C_{BC}$ of implementing the calcium carbonate scale inhibition program for the total number $X_T$ of hydrocarbon wells 128 using the calcium carbonate scale inhibition chemical. For example, if the machine learning method having the lowest cost metric $C_P$ is more expensive than the base cost $C_{BC}$, the scale inhibition program can be designed using the base cost scenario.

The display device 124 displays results of the processing by the processors 108 to a user. The display device 124 is illustrated and described below with reference to FIG. 5. If the lowest cost metric $C_P$ is less than the base cost $C_{BC}$, the computer system 100 presents the machine learning method having the lowest cost metric $C_P$ using the display device 124 of the computer system 100.

Machine Learning Framework for Prediction of Calcium Carbonate Scale

Figure 2:
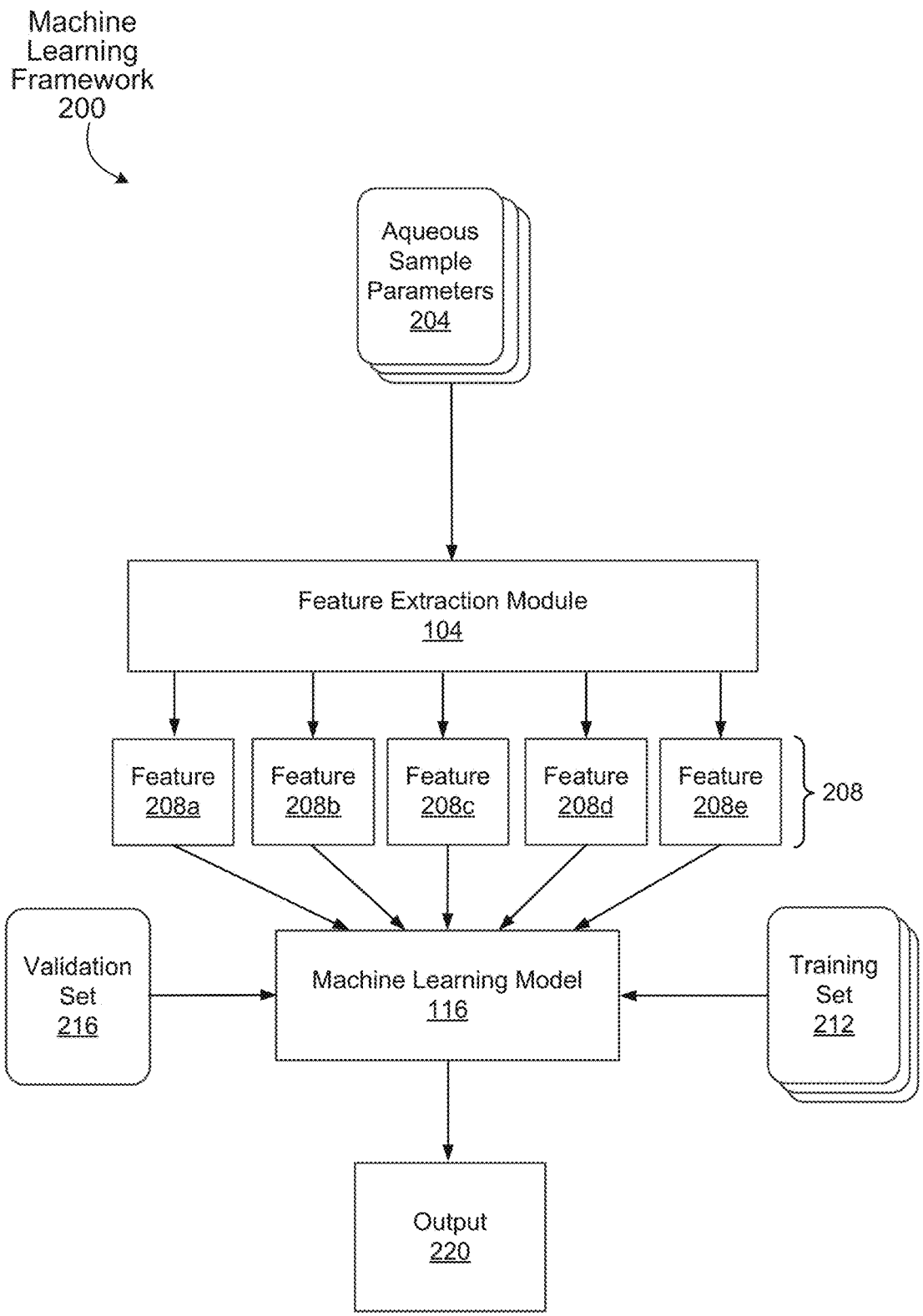
FIG. 2 shows a machine learning framework for prediction and inhibition of calcium carbonate scale in hydrocarbon wells, in accordance with one or more embodiments.

FIG. 2 shows a machine learning framework 200 for prediction and inhibition of calcium carbonate scale in hydrocarbon wells, in accordance with one or more embodiments. Among other components and parts, the machine learning framework 200 includes aqueous sample parameters 204, the feature extraction module 104, the machine learning model 116, a validation 216, and a training set 212.

The computer system 100 extracts the training data 120 including one or more parameters 204 from the aqueous samples 132, as described above with reference to FIG. 1. Each aqueous sample 132 is collected from a respective hydrocarbon well of a plurality of hydrocarbon wells 128. The feature extraction module 104 determines a feature vector 208 from the labeled training data 120 as described above with reference to FIG. 1. The feature vector 208 is determined based on the one or more parameters 204 extracted from the aqueous samples 132. The feature vector 208 is indicative of whether the respective hydrocarbon well 128 contains calcium carbonate scale.

For example, a feature 208a of the feature vector 208 can include the water saturation level SL of one or more aqueous samples 132. A feature 208b of the feature vector 208 can include the Langelier Saturation Index of one or more aqueous samples 132. A feature 208c of the feature vector 208 can include the Ryznar Saturation Index of one or more aqueous samples 132. A feature 208d of the feature vector 208 can include the Puckorius Scaling Index of one or more aqueous samples 132. A feature 208e of the feature vector 208 can include the calcium carbonate saturation index SI of one or more aqueous samples 132.

In some embodiments, the computer system 100 segregates or divides the labeled training data 120, prior to the determining of the feature vector 208, into a training set 212 and a validation set 216. The feature vector 208 used for training the machine learning model 116 is determined from the training set 212. For example the labeled training data 120 can be divided such that 80% of the training data 120 comprises the training set 212 and 20% of the training data 120 comprises the validation set 216. The computer system 100 determines the accuracy of the machine learning model 116 by testing the trained machine learning model 116 against the validation set 216.

In some embodiments, the computer system 100 forms the training set 212 of features and training labels by identifying a positive set of features that have been determined to have the property in question (correct indication of scale formation), and, in some embodiments, forms a negative set of features that lack the property in question. In some embodiments, the validation set 216 is formed of additional features, other than those in the training set 212, which have already been determined to have or to lack the property in question. The computer system 100 applies the trained machine learning model 116 to the features 208 of the validation set 216 to quantify the accuracy of the machine learning model 116. Metrics applied in accuracy measurement can include: Precision=TP/(TP+FP) and Recall=TP/(TP+FN), where Precision is how many results the machine learning model 116 correctly predicted (TP or true positives) out of the total it predicted (TP+FP or false positives), and Recall is how many results the machine learning model 116 correctly predicted (TP) out of the total number of features that did have the property in question (TP+FN or false negatives). An F-score (F-score=2×PR/(P+R)) unifies Precision and Recall into a single measure. In some embodiments, the computer system 100 iteratively re-trains the machine learning model 116 until the occurrence of a stopping condition, such as an accuracy measurement indication that the machine learning model 116 is sufficiently accurate, or a sufficient number of training rounds having taken place.

The output 220 of the machine learning model 116, when executed, on new features 208 is the number of hydrocarbon wells containing scale within a particular time period. In some embodiments, the output 220 indicates whether a particular hydrocarbon well contains scale. In some alternative embodiments, the machine learning model 116 (in the form of a CNN) can generate the output 220, without the need for explicit feature extraction. A CNN is a feed-forward artificial neural network in which the connectivity pattern between its neurons is inspired by the organization of a visual cortex. The advantage of a CNN includes the obviation of explicit feature extraction and the use of shared weight in convolutional layers, which means that the same filter (weights bank) is used for each element in the layer; this both reduces memory footprint and improves performance.

Process for Prediction of Calcium Carbonate Scale in Hydrocarbon Wells

FIG. 3 shows a process 300 for prediction of calcium carbonate scale in hydrocarbon wells using machine learning, in accordance with one or more embodiments.

The computer system 100 extracts 304 training data (e.g., the training data 120). The training data 120 includes one or more parameters (e.g., the parameters 204) from each aqueous sample of a plurality of aqueous samples (e.g., the aqueous samples 132). Each of the aqueous samples 132 is collected from a respective hydrocarbon well of a plurality of hydrocarbon wells (e.g., the hydrocarbon wells 128). The parameters can include the ionic composition of the aqueous samples 132.

The computer system 100 classifies 308 the training data 120 in accordance with hydrocarbon production conditions of each hydrocarbon well 128. In some embodiments, the hydrocarbon production conditions include a hydrocarbon flow rate, a hydrocarbon pressure, a temperature, or a composition of brine, oil, and gas of the hydrocarbon well 128.

The computer system 100 labels 312 the classified training data 120 in accordance with whether calcium carbonate scale has formed in each aqueous sample of the plurality of aqueous samples 132 within a particular time period. For example, the time period selected can be 10 years.

The computer system 100 determines 316 a feature vector (e.g., the feature vector 208) from the labeled training data 120. The feature vector 208 is determined based on the one or more parameters 204 extracted from the aqueous samples 132. The feature vector 208 is indicative of whether a respective hydrocarbon well contains calcium carbonate scale.

The computer system 100 generates 320 a trained machine learning model (e.g., the machine learning model 116). The machine learning model 116 is trained based on the feature vector 208 to predict a number of the hydrocarbon wells 128 containing calcium carbonate scale within the particular time period.

Process for Prediction of Calcium Carbonate Scale in Hydrocarbon Wells

FIG. 4 shows a process 400 for inhibition of calcium carbonate scale in hydrocarbon wells using machine learning, in accordance with one or more embodiments.

The computer system 100 generates 404 a confusion matrix for each machine learning method of the plurality of machine learning methods. The confusion matrix is generated by executing the machine learning model 116. The machine learning model 116 is trained, using each machine learning method, to predict a number of the hydrocarbon wells 128 containing calcium carbonate scale. The machine learning model 116 is trained based on the one or more parameters 204 extracted from the aqueous samples 132 collected from the hydrocarbon wells 128.

The computer system 100 generates 408 a probabilistic model indicating an uncertainty associated with using each machine learning method to predict the number of hydrocarbon wells 128 containing calcium carbonate scale based on the confusion matrix.

The computer system 100 generates 412 a cost metric $C_P$ indicating a cost of implementing a calcium carbonate scale inhibition program using each machine learning method based on the probabilistic model.

The computer system 100 selects 416 a machine learning method of the several machine learning methods that has the lowest cost metric $C_P$.

The computer system 100 determines 420 whether the lowest cost metric $C_P$ is less than the base cost $C_{BC}$. The base cost $C_{BC}$ is the cost of implementing the calcium carbonate scale inhibition program for the total number $X_T$ of hydrocarbon wells 128 using a calcium carbonate scale inhibition chemical.

Responsive to the lowest cost metric $C_P$ being less than the base cost $C_{BC}$, the computer system 100 presents 424 the machine learning method having the lowest cost metric $C_P$ using a display device (e.g., the display device 124) of the computer system 100.

Figure 5:
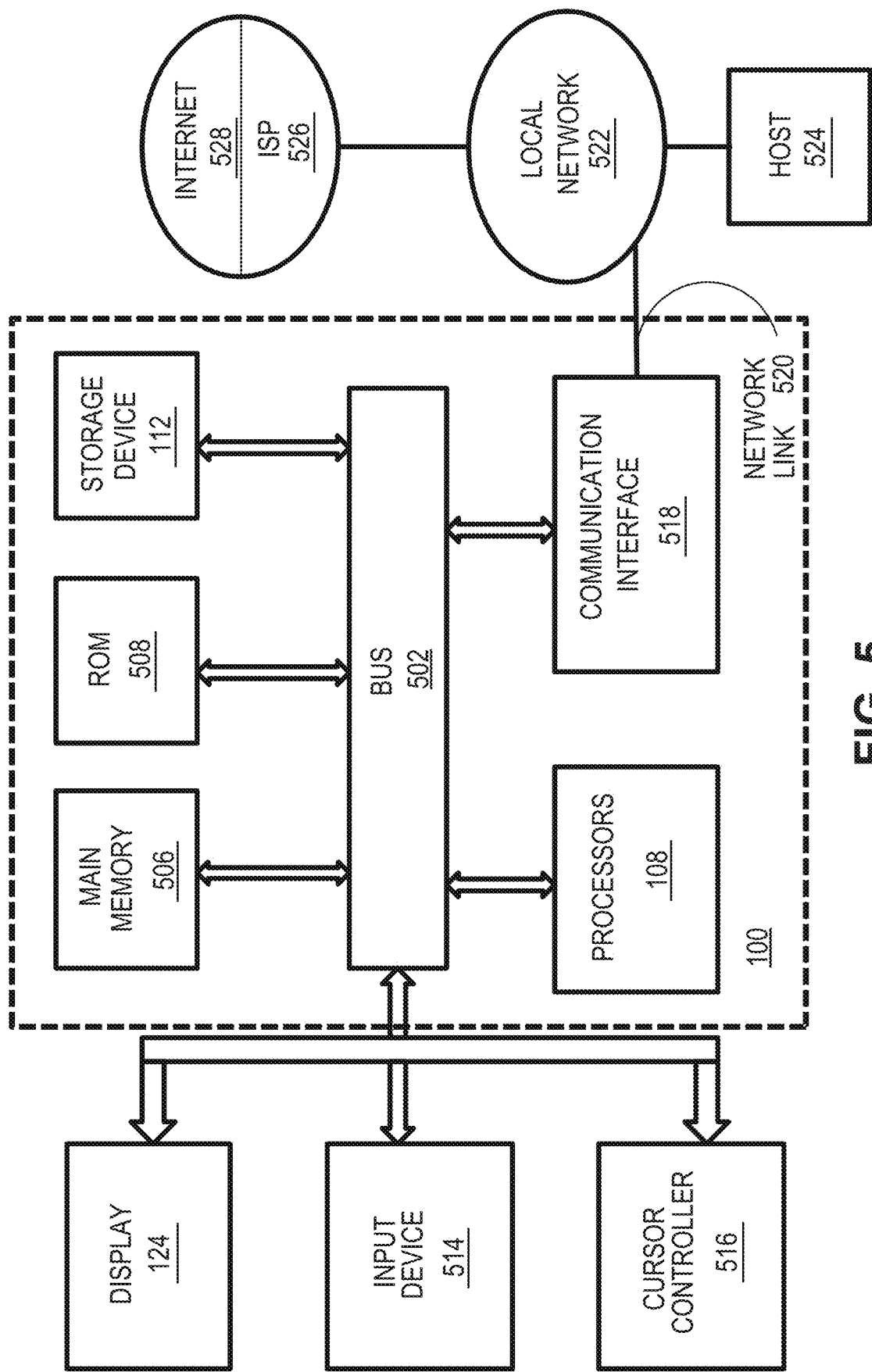
FIG. 5 shows an example implementation of a computer system for prediction and inhibition of calcium carbonate scale in hydrocarbon wells using machine learning, in accordance with one or more embodiments.

Example Implementation of Computer System for Prediction of Calcium Carbonate Scale FIG. 5 shows an example implementation of the computer system 100, in accordance with one or more embodiments. In the example implementation, the computer system 100 is a special purpose computing device. The special-purpose computing device is hard-wired to perform prediction of calcium carbonate scale or includes digital electronic devices such as one or more application-specific integrated circuits (ASICs) or field programmable gate arrays (FPGAs) that are persistently programmed to perform the techniques herein, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. In various embodiments, the special-purpose computing devices are desktop computer systems, portable computer systems, handheld devices, network devices or any other device that incorporates hard-wired and/or program logic to implement the techniques.

In an embodiment, the computer system 100 includes a bus 502 or other communication mechanism for communicating information, and one or more computer hardware processors 108 coupled with a bus 502 for processing information. The hardware processors 108 are, for example, general-purpose microprocessors. The computer system 100 also includes a main memory 506, such as a random-access memory (RAM) or other dynamic storage device, coupled to the bus 502 for storing information and instructions to be executed by processors 108. In one implementation, the main memory 506 is used for storing temporary variables or other intermediate information during execution of instructions to be executed by the processors 108. Such instructions, when stored in non-transitory storage media accessible to the processors 108, render the computer system 100 into a special-purpose machine that is customized to perform the operations specified in the instructions.

In an embodiment, the computer system 100 further includes a read only memory (ROM) 508 or other static storage device coupled to the bus 502 for storing static information and instructions for the processors 108. A storage device 112, such as a magnetic disk, optical disk, solid-state drive, or three-dimensional cross point memory is provided and coupled to the bus 502 for storing information and instructions.

In an embodiment, the computer system 100 is coupled via the bus 502 to a display 124, such as a cathode ray tube (CRT), a liquid crystal display (LCD), plasma display, light emitting diode (LED) display, or an organic light emitting diode (OLED) display for displaying information to a computer user. An input device 514, including alphanumeric and other keys, is coupled to bus 502 for communicating information and command selections to the processors 108. Another type of user input device is a cursor controller 516, such as a mouse, a trackball, a touch-enabled display, or cursor direction keys for communicating direction information and command selections to the processors 108 and for controlling cursor movement on the display 124. This input device typically has two degrees of freedom in two axes, a first axis (e.g., x-axis) and a second axis (e.g., y-axis), that allows the device to specify positions in a plane.

According to one embodiment, the techniques herein are performed by the computer system 100 in response to the processors 108 executing one or more sequences of one or more instructions contained in the main memory 506. Such instructions are read into the main memory 506 from another storage medium, such as the storage device 112. Execution of the sequences of instructions contained in the main memory 506 causes the processors 108 to perform the process steps described herein. In alternative embodiments, hard-wired circuitry is used in place of or in combination with software instructions.

The term "storage media" as used herein refers to any non-transitory media that store data and/or instructions that cause a machine to operate in a specific fashion. Such storage media includes non-volatile media and/or volatile media. Non-volatile media includes, for example, optical disks, magnetic disks, solid-state drives, or three-dimensional cross point memory, such as the storage device 112. Volatile media includes dynamic memory, such as the main memory 506. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NV-RAM, or any other memory chip or cartridge.

Storage media is distinct from but may be used in conjunction with transmission media. Transmission media participates in transferring information between storage media. For example, transmission media includes coaxial cables, copper wire and fiber optics, including the wires that comprise the bus 502. Transmission media can also take the form of acoustic or light waves, such as those generated during radio-wave and infrared data communications.

In an embodiment, various forms of media are involved in carrying one or more sequences of one or more instructions to the processors 108 for execution. For example, the instructions are initially carried on a magnetic disk or solid-state drive of a remote computer. The remote computer loads the instructions into its dynamic memory and send the instructions over a telephone line using a modem. A modem local to the computer system 100 receives the data on the telephone line and use an infrared transmitter to convert the data to an infrared signal. An infrared detector receives the data carried in the infrared signal and appropriate circuitry places the data on the bus 502. The bus 502 carries the data to the main memory 506, from which processors 108 retrieves and executes the instructions. The instructions received by the main memory 506 may optionally be stored on the storage device 112 either before or after execution by processors 108.

The computer system 100 also includes a communication interface 518 coupled to the bus 502. The communication interface 518 provides a two-way data communication coupling to a network link 520 that is connected to a local network 522. For example, the communication interface 518 is an integrated service digital network (ISDN) card, cable modem, satellite modem, or a modem to provide a data communication connection to a corresponding type of telephone line. As another example, the communication interface 518 is a local area network (LAN) card to provide a data communication connection to a compatible LAN. In some implementations, wireless links are also implemented. In any such implementation, the communication interface 518 sends and receives electrical, electromagnetic, or optical signals that carry digital data streams representing various types of information.

The network link 520 typically provides data communication through one or more networks to other data devices. For example, the network link 520 provides a connection through the local network 522 to a host computer 524 or to a cloud data center or equipment operated by an Internet Service Provider (ISP) 526. The ISP 526 in turn provides data communication services through the world-wide packet data communication network now commonly referred to as the "Internet" 528. The local network 522 and Internet 528 both use electrical, electromagnetic or optical signals that carry digital data streams. The signals through the various networks and the signals on the network link 520 and through the communication interface 518, which carry the digital data to and from the computer system 100, are example forms of transmission media. In an embodiment, the network 520 contains the cloud 502 or a part of the cloud 502 described above.

The computer system 100 sends messages and receives data, including program code, through the network(s), the network link 520, and the communication interface 518. In an embodiment, the computer system 100 receives code for processing. The received code is executed by the processors 108 as it is received, and/or stored in storage device 112, or other non-volatile storage for later execution.

What is claimed is:

1. A method comprising:
    extracting, using a computer system, training data comprising one or more parameters from each aqueous sample of a plurality of aqueous samples, wherein each aqueous sample includes a fluid and is collected from a respective hydrocarbon well of a plurality of hydrocarbon wells;
    classifying, using the computer system, the training data in accordance with hydrocarbon production conditions of each hydrocarbon well;
    labeling, using the computer system, the classified training data in accordance with whether calcium carbonate scale has formed in each aqueous sample of the plurality of aqueous samples within a particular time period;
    determining, using the computer system, a feature vector from the labeled, classified training data based on the one or more parameters extracted from the each aqueous sample of the plurality of aqueous samples, wherein the feature vector is indicative of whether the respective hydrocarbon well contains calcium carbonate scale; and
    generating, using the computer system, a trained machine learning model, wherein the machine learning model is trained based on the feature vector, to predict a number of hydrocarbon wells of the plurality of hydrocarbon wells containing calcium carbonate scale within the particular time period.

2. The method of claim 1, wherein the hydrocarbon production conditions comprise a hydrocarbon flow rate of the each hydrocarbon well, a hydrocarbon pressure of the each hydrocarbon well, a temperature of the each hydrocarbon well, and a composition of brine, oil, and gas of the each hydrocarbon well.

3. The method of claim 1, further comprising:
    selecting, using the computer system, the particular time period based on a type of a calcium carbonate scale inhibition chemical and a chemical residue life of the calcium carbonate scale inhibition chemical,
    wherein the calcium carbonate scale inhibition chemical is used to inhibit formation of the calcium carbonate scale in the each aqueous sample.

4. The method of claim 1, wherein the feature vector indicates a level of carbonate equilibrium of the each aqueous sample of the plurality of aqueous samples estimated based on the one or more parameters extracted from the each aqueous sample.

5. The method of claim 1, wherein the determining of the feature vector comprises at least one of:
    estimating, using the computer system, a water saturation level of the each aqueous sample of the plurality of aqueous samples from the labeled training data;
    estimating, using the computer system, a Langelier Saturation Index of the each aqueous sample of the plurality of aqueous samples from the labeled training data;
    estimating, using the computer system, Ryznar Saturation Index of the each aqueous sample of the plurality of aqueous samples from the labeled training data; or
    estimating, using the computer system, a Puckorius Scaling Index of the each aqueous sample of the plurality of aqueous samples from the labeled training data.

6. The method of claim 1, further comprising:
    segregating, using the computer system, the labeled training data, prior to the determining of the feature vector, into a training set and a validation set, wherein the feature vector is determined from the training set; and
    testing, using the computer system, the trained machine learning model against the validation set.

7. The method of claim 1, wherein the generating of the trained machine learning model comprises:
    training the machine learning model, based on the feature vector, to predict the number of hydrocarbon wells of the plurality of hydrocarbon wells containing calcium carbonate scale within the particular time period using at least one of a k-nearest neighbors method, a support vector machine, gradient boosting, a gradient boosting classifer, or a decision tree classifier.

8. A non-transitory computer-readable storage medium storing instructions executable by a computer system, the instructions when executed by the computer system cause the computer system to:
    extract training data comprising one or more parameters from each aqueous sample of a plurality of aqueous samples, wherein the each aqueous sample includes a fluid and is collected from a different hydrocarbon well of a plurality of hydrocarbon wells;
    classify the training data in accordance with hydrocarbon production conditions of each hydrocarbon well of the plurality of hydrocarbon wells;

label the classified training data in accordance with whether calcium carbonate scale has formed in each aqueous sample of the plurality of aqueous samples within a particular time period;

determine a feature vector from the labeled training data based on the one or more parameters extracted from the each aqueous sample of the plurality of aqueous samples; and generate a trained machine learning model, wherein the machine learning model is trained based on the feature vector, to predict a number of hydrocarbon wells of the plurality of hydrocarbon wells containing calcium carbonate scale within the particular time period.

9. The non-transitory computer-readable storage medium of claim 8, wherein the hydrocarbon production conditions comprise a hydrocarbon flow rate of the each hydrocarbon well, a hydrocarbon pressure of the each hydrocarbon well, a temperature of the each hydrocarbon well, and a composition of brine, oil, and gas of the each hydrocarbon well.

10. The non-transitory computer-readable storage medium of claim 8, wherein the instructions further cause the computer system to:
select the particular time period based on a type of a calcium carbonate scale inhibition chemical and a chemical residue life of the calcium carbonate scale inhibition chemical, wherein the calcium carbonate scale inhibition chemical is used to inhibit formation of the calcium carbonate scale in the each aqueous sample.

11. The non-transitory computer-readable storage medium of claim 8, wherein the feature vector indicates a level of carbonate equilibrium of the each aqueous sample of the plurality of aqueous samples estimated based on the one or more parameters extracted from the each aqueous sample.

12. The non-transitory computer-readable storage medium of claim 8, wherein the determining of the feature vector comprises at least one of:
estimating a water saturation level of the each aqueous sample of the plurality of aqueous samples from the labeled training data;
estimating a Langelier Saturation Index of the each aqueous sample of the plurality of aqueous samples from the labeled training data;
estimating Ryznar Saturation Index of the each aqueous sample of the plurality of aqueous samples from the labeled training data; or
estimating a Puckorius Scaling Index of the each aqueous sample of the plurality of aqueous samples from the labeled training data.

13. The non-transitory computer-readable storage medium of claim 8, wherein the instructions further cause the computer system to:
segregate the labeled training data, prior to the determining of the feature vector, into a training set and a validation set, wherein the feature vector is determined from the training set; and
test the trained machine learning model against the validation set.

14. The non-transitory computer-readable storage medium of claim 8, wherein the generating of the trained machine learning model comprises:
training the machine learning model, based on the feature vector, to predict the number of hydrocarbon wells of the plurality of hydrocarbon wells containing calcium carbonate scale within the particular time period using at least one of a k-nearest neighbors method, a support vector machine, gradient boosting, a gradient boosting classifer, or a decision tree classifier.

15. A computer system comprising:
one or more computer processors; and
a non-transitory computer-readable storage medium storing instructions executable by the one or more computer processors, the instructions when executed by the one or more computer processors cause the one or more computer processors to:
extract training data comprising one or more parameters from each aqueous sample of a plurality of aqueous samples, wherein each aqueous sample includes a fluid and is collected from a different hydrocarbon well of a plurality of hydrocarbon wells;
classify the training data in accordance with hydrocarbon production conditions of each hydrocarbon well of the plurality of hydrocarbon wells;
label the classified training data in accordance with whether calcium carbonate scale has formed in each aqueous sample of the plurality of aqueous samples within a particular time period;
determine a feature vector from the labeled, classified training data based on the one or more parameters extracted from the each aqueous sample of the plurality of aqueous samples; and
generate a trained machine learning model, wherein the machine learning model is trained based on the feature vector, to predict a number of hydrocarbon wells of the plurality of hydrocarbon wells containing calcium carbonate scale within the particular time period.

16. The computer system of claim 15, wherein the hydrocarbon production conditions comprise a hydrocarbon flow rate of the each hydrocarbon well, a hydrocarbon pressure of the each hydrocarbon well, a temperature of the each hydrocarbon well, and a composition of brine, oil, and gas of the each hydrocarbon well.

17. The computer system of claim 15, wherein the instructions further cause the one or more computer processors to:
select the particular time period based on a type of a calcium carbonate scale inhibition chemical and a chemical residue life of the calcium carbonate scale inhibition chemical, wherein the calcium carbonate scale inhibition chemical is used to inhibit formation of the calcium carbonate scale in the each aqueous sample.

18. The computer system of claim 15, wherein the feature vector indicates a level of carbonate equilibrium of the each aqueous sample of the plurality of aqueous samples estimated based on the one or more parameters extracted from the each aqueous sample.

19. The computer system of claim 15, wherein the determining of the feature vector comprises at least one of:
estimating a water saturation level of the each aqueous sample of the plurality of aqueous samples from the labeled training data;
estimating a Langelier Saturation Index of the each aqueous sample of the plurality of aqueous samples from the labeled training data;
estimating Ryznar Saturation Index of the each aqueous sample of the plurality of aqueous samples from the labeled training data; or
estimating a Puckorius Scaling Index of the each aqueous sample of the plurality of aqueous samples from the labeled training data.

20. The computer system of claim 15, wherein the instructions further cause the one or more computer processors to:
- segregate the labeled training data, prior to the determining of the feature vector, into a training set and a validation set, wherein the feature vector is determined from the training set; and
- test the trained machine learning model against the validation set.

\* \* \* \* \*

UNITED STATES PATENT AND TRADEMARK OFFICE
CERTIFICATE OF CORRECTION

| | |
|---|---|
| PATENT NO. | : 11,867,027 B2 |
| APPLICATION NO. | : 16/410690 |
| DATED | : January 9, 2024 |
| INVENTOR(S) | : Nasser Mubarak Al-Hajri, Abdullah Abdulaziz AlGhamdi and Fahad Muhammed Al-Meshal |

It is certified that error appears in the above-identified patent and that said Letters Patent is hereby corrected as shown below:

In the Claims

In Column 18, Line 55, Claim 7, please replace "classifer" with -- "classifier" --

In Column 18, Line 62, Claim 8, before "each" delete "the"

In Column 19, Line 5, Claim 8, please replace "the labeled" with -- "the labeled, classified" --

In Column 20, Line 2, Claim 14, please replace "classifer" with -- "classifier" --

Signed and Sealed this
Twenty-seventh Day of February, 2024

Katherine Kelly Vidal
*Director of the United States Patent and Trademark Office*